United States Patent [19]

Cragoe, Jr. et al.

[11] 3,976,686

[45] Aug. 24, 1976

[54] [1-OXO-2,3-HYDROCARBYLENE-5-INDANYLOXY(OR THIO)]ALKANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: Sept. 21, 1973

[21] Appl. No.: 399,568

[30] Foreign Application Priority Data
Oct. 13, 1972  Canada .................................. 153921
Aug. 28, 1973  Canada .................................. 178825

[52] U.S. Cl. .......................... 260/520 C; 260/308 D; 260/470; 260/473 F; 260/516; 260/558.5; 260/559 B; 424/269; 424/308; 424/317; 424/324
[51] Int. Cl.$^2$ ..................... C07C 63/44; C07C 69/95
[58] Field of Search ........................ 260/520, 473 F

[56] References Cited

OTHER PUBLICATIONS

Bair Diss. Abst. 3244 (1961).

*Primary Examiner*—Norman Morgenstern
*Attorney, Agent, or Firm*—Michael C. Sudol, Jr.; J. Jerome Behan

[57] ABSTRACT

[1-Oxo-2,3-hydrocarbylene-5-indanyloxy(or thio)] alkanoic acids, and the non-toxic pharmaceutically acceptable salts, esters and amides thereof are disclosed. The products display a polyfunctional pharmaceutical utility in that they exhibit diuretic, saluretic, uricosuric and antihypertensive activity. Also disclosed are processes for the preparation of such compounds, and methods of treatment comprising administering such compounds and compositions.

6 Claims, No Drawings

[1-OXO-2,3-HYDROCARBYLENE-5-INDANYLOXY(OR THIO)]ALKANOIC ACIDS

BACKGROUND OF THE INVENTION

This invention relates to a new class of chemical compounds which can be described generally as [1-oxo-2,3-hydrocarbylene-5-indanyloxy(and thio)]alkanoic acids, and the nontoxic pharmaceutically acceptable salts, esters and amides thereof. Further, this invention relates to methods for the preparation of such compounds, pharmaceutical compositions comprising such compounds and to methods of treatment comprising administering such compositions and compounds.

Pharmacological studies show that the instant compounds are effective diuretic and saluretic agents which can be used in the treatment of conditions associated with electrolyte and fluid retention. The instant compounds are also useful in the treatment of hypertension. In addition, these compounds are able to maintain the uric acid concentration in the body at pretreatment levels or to even effect a decrease in the uric acid concentration.

The compounds of this invention may be described more fully by the following general representation:

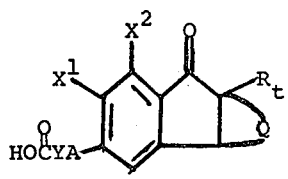

wherein A is oxygen or sulfur; $X^1$ is selected from hydrogen, halogen such as fluoro, bromo, chloro, iodo and the like, and methyl, $X^2$ is halogen, such as fluoro, chloro, bromo and iodo, methyl and trifluoromethyl, and taken together, the two X radicals may be joined to form a hydrocarbylene chain containing from 1 to 4 carbon atoms between their points of attachment, for example, trimethylene, tetramethylene, and 1,3-butadieneylene; Y is an alkylene or haloalkylene radical having a maximum of 4 carbon atoms as for example methylene, ethylene, propylidene, isopropylidene, isobutylidene, fluoromethylene and the like; R is hydrogen, or lower alkyl for example methyl, ethyl, propyl, isopropyl, butyl and the like; wherein the subscript $t$ is either 1 or 0; and wherein Q represents a hydrocarbylene bridge containing, together with the carbon atoms of the indane nucleus to which they are attached, from 3 to 6 carbon atoms; and forming a hydrocarbylene ring which is either unsaturated, or saturated. The invention also includes the pharmaceutically acceptable salts, the lower alkyl ester, the amides and the derivatives where carboxy is replaced by 5-tetrazolyl.

For conceptual convenience the above described compounds of this invention may be considered as 2,3-hydrocarbylene derivatives of substituted 5-indanyloxyalkanoic acids.

When administered in therapeutic dosages, in conventional vehicles, the instant [1-oxo-2,3-hydrocarbylene-5-indanyloxy(and thio)] alkanoic acids effectively reduce the amount of sodium and chloride ions in the body, lower dangerous excesses of fluid levels and in general alleviate conditions usually associated with edema. In addition these compounds overcome a major problem associated with many of the presently available diuretics and saluretics. Many of the presently available diuretics and saluretics have a tendency upon administration to induce hyperuricemia which may precipitate uric acid or sodium urate or both in the body which may cause from mild to severe cases of gout. Thus the [1-oxo-2,3-hydrocarbylene-5-indanyloxy(and thio)]alkanoic acids of this invention provide an effective tool to treat those patients requiring diuretic and saluretic treatment without incurring the risk of inducing gout. Further the [1-oxo-2,5-hydrocarbylene-5-indanyloxy(and thio)]alkanoic acids of this invention are effective antihypertensive agents.

Thus it is an object of this invention to provide 2,3-hydrocarbylene indanes of the above description which offer diuretic, saluretic, uricosuric and antihypertensive activities.

It is also an object of this invention to provide processes for the preparation of such [1-oxo-2,3-hydrocarbylene-5-indanyloxy(and thio)]alkanoic acid indanes and to provide pharmaceutical compositions comprising a therapeutically effective amount of such compounds and to provide a method of treatment comprising administering such compounds and compositions.

SUMMARY OF THE INVENTION

In its product aspect this invention relates to [1-oxo-2,3-hydrocarbylene-5-indanyloxy(and thio)]alkanoic acids having diuretic, saluretic, uricosuric and antihypertensive pharmacological properties of the following formula along with the pharmaceutically acceptable salts thereof:

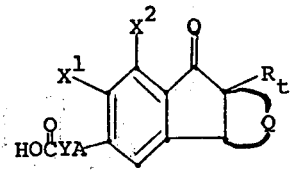

wherein A is oxygen or sulfur; Y is an alkylene or halo alkylene radical having a maximum of 4 carbon atoms; $X^1$ is selected from hydrogen, halogen and methyl; $X^2$ is halogen or methyl and $X^1$ and $X^2$ may be joined to form a hydrocarbylene chain containing from 1 to 4 carbon atoms; $R_t$ is H or lower alkyl and the subscript $t$ is either 0 or 1; Q represents a hydrocarbylene chain and contains, together with the carbon atoms of the indane nucleus, from 3 to 6 carbon atoms and is unsaturated, or saturated.

Pharmaceutical compositions comprising therapeutically effective amounts of such [1-oxo-2,3-hydrocarbylene-5-indanyloxy(and thio)alkanoic acids and methods of treatment comprising administering such compositions and compounds for the alleviation of edema, hyperuricemia and hypertension are described in detail below.

DETAILED DESCRIPTION OF THE INVENTION

Particularly preferred embodiments of the diuretic 2,3-hydrocarbylene indanes of this invention are those having the following structural formula:

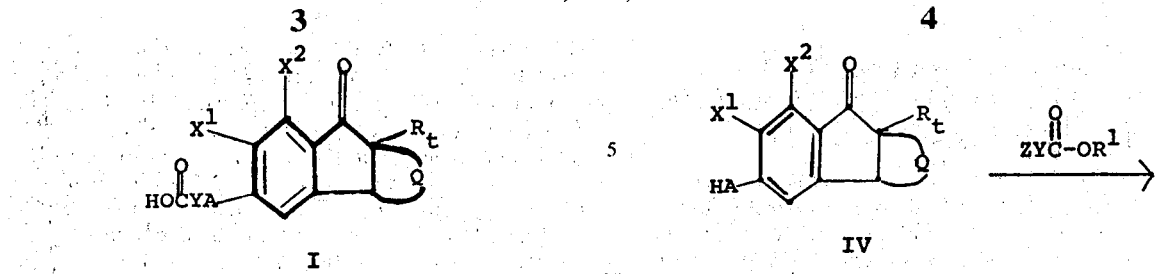

wherein $X^2$ is methyl or chloro; $X^1$ is hydrogen, methyl or chloro; R is H, or lower alkyl having from 1 to 4 carbon atoms and the subscript $t$ is either 0 or 1; the hydrocarbylene group, Q is methylene, ethylene, trimethylene, tetramethylene or 1,4-butadienylene.

The [1-oxo-2,3-hydrocarbylene-5-indanyloxy(and thio)]alkanoic acids wherein the hydrocarbylene is methylene (III) may be prepared by the 1,1′-cyclo addition of a carbene or ylide to an appropriately substituted [1-oxoinden-5-yloxy(or thio)]alkanoic acid (II), according to the following reaction:

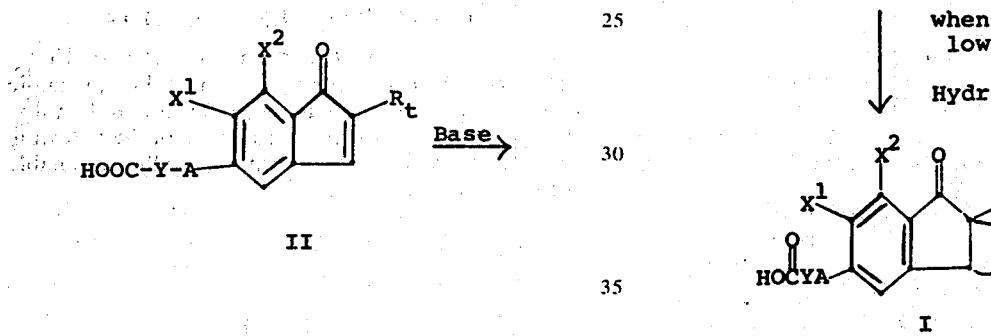

wherein all substituents are as defined above. The (1-oxoindene-5-yloxy)alkanoic acids employed are described in U.S. Pat. No. 3,668,241.

The [1-oxo-2,3-hydrocarbylene-5-indanyloxy(and thio)]alkanoic acids and ester (I) wherein Y contains 1 or 3 linear carbon atoms may be prepared by an etherification method which comprises reacting a haloacetic acid or ester thereof of the formula:

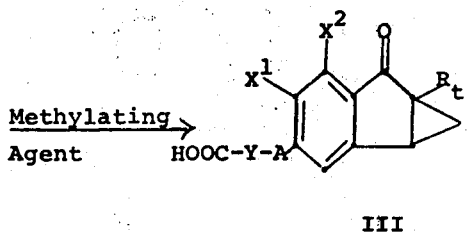

wherein $R^1$ is hydrogen or lower alkyl such as methyl, ethyl and the like and Z is halo such as bromo, chloro, iodo and the like with a suitable 2,3-hydrocarbylene-5-hydroxy(or mercapto)-1-indanone (IV, infra). The following equation illustrates this reaction:

wherein $X^1$, $X^2$, R, $R^1$, A, Q, Y, Z and $t$ are as defined above; In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25°C. to the reflux temperature of the particular solvent employed. The reaction with the haloacetic acid or ester is generally complete in about 10 to 60 minutes. If the haloacetic acid ester is employed, the ester obtained may be hydrolyzed to the free acid by methods well known to those skilled in the art.

Those [1-oxo-2,3-hydrocarbylene-5-indanyloxy(or thio)]alkanoic acids (I) wherein the alkylene chain contains 2 linear carbon atoms between the carboxy and oxy (or thio) groups are prepared from their corresponding 2,3-hydrocarbylene-5-hydroxy-(or mercapto)-1-indanones (IV) by the reaction of the latter with propiolactone or with an appropriately substituted propiolactone, in the presence of a base such as aqueous solution of sodium hydroxide, preferably, while heating the solution at reflux temperatures; followed by the acidification of the carboxylate intermediate thus formed to the desired acid. The following equation illustrates the reaction:

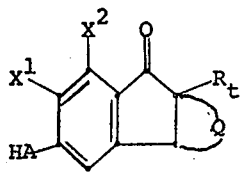

IV

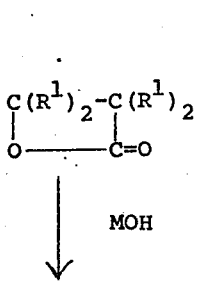

↓ MOH

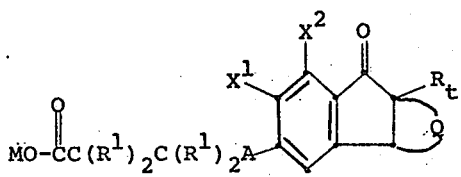

Ic

↓ Acidification

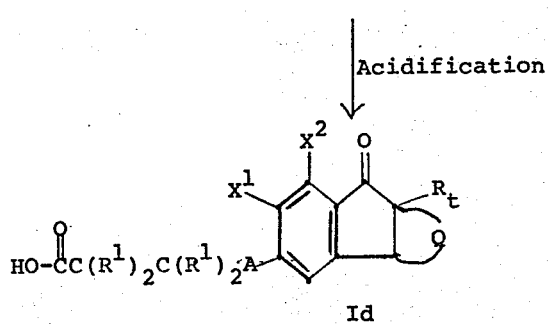

Id wherein A, Q, $t$, R, $R^1$, $X^1$ and $X^2$ are as defined above and M is a cation derived from an alkali metal hydroxide or akali metal carbonate such as a sodium or potassium cation.

The 2,3-hydrocarbylene-5-hydroxy-(or mercapto)-1-indanones (IV, supra), which also exhibit diuretic and uricosuric activity, are prepared by treating the correspondingly substituted 2,3-hydrocarbylene-5-lower alkoxy (or lower alkylthio)-1-indanone with an ether cleaving reagent such as aluminum chloride, pyridine hydrochloride, sodium in liquid ammonia and the like. When aluminum chloride is employed, the solvent may be heptane, carbon disulfide, methyl chloride and the like and when pyridine hydrochloride is employed, it is not necessary to employ a solvent. The following equation illustrates this process:

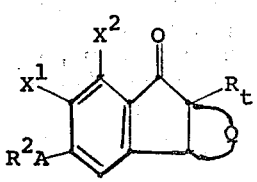

V

Ether Cleavage →

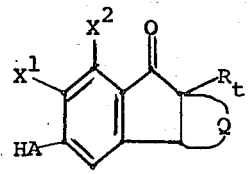

IV wherein A, Q, $t$, R, $R^1$, $X^1$ and $X^2$ are as defined above, and $R^2$ is lower alkyl.

The 2-substituted-2,3-hydrocarbylene-5-loweralkoxy-(or lower alkyl thio)-1-indanones (V, supra) which exhibit uricosuric activity are prepared by treating a 2,3-hydrocarbylene-5-lower alkoxy-(or lower alkyl thio)-1-indanone (VI, infra) with a suitable alkylating reagent of the formula: R Z wherein R and Z are as defined above. This reaction is conducted by first treating the 2,3-hydrocarbylene-5-lower alkoxy-1-indanone (VI) with a suitable base, for example, an alkali metal hydride such as sodium hydride and the like, or an alkali metal alkoxide, for example, potassium tertiary butoxide and the like. Other bases which may be employed include sodium amide, lithium amide and the like. This basified compound is then treated with the alkylating reagent, R Z. Any solvent which is inert or substantially inert to the reactants employed may be used. Suitable solvents include, for example, 1-2-dimethoxyethane, tertiary butanol, benzene, dimethylformamide and the like. The reaction may be conducted at a temperature in the range of from about 25° to about 150°C. In general, the reaction is conducted at a temperature in the range of from about 75° to about 90°C. The following equation illustrates this process:

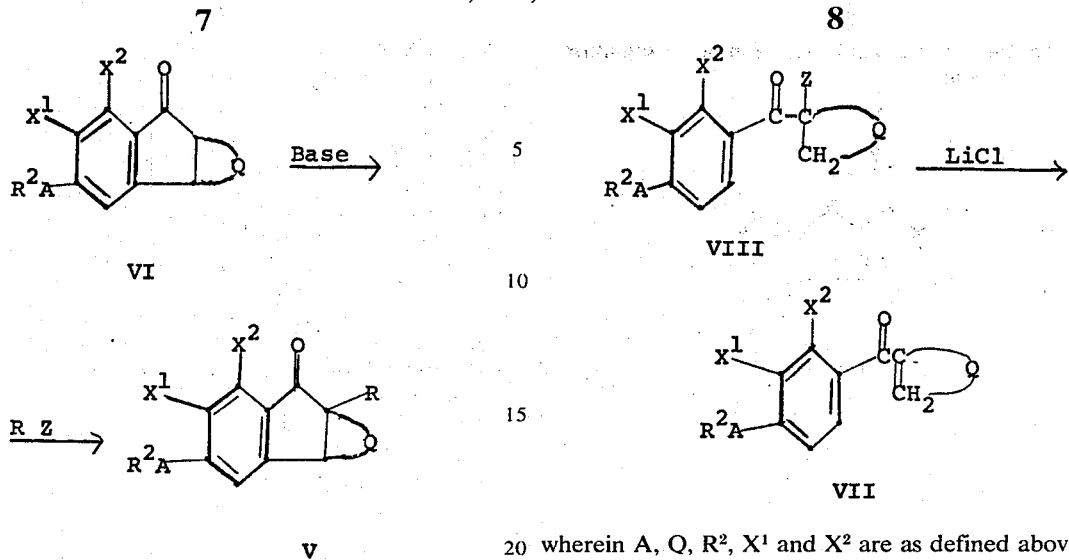

VI

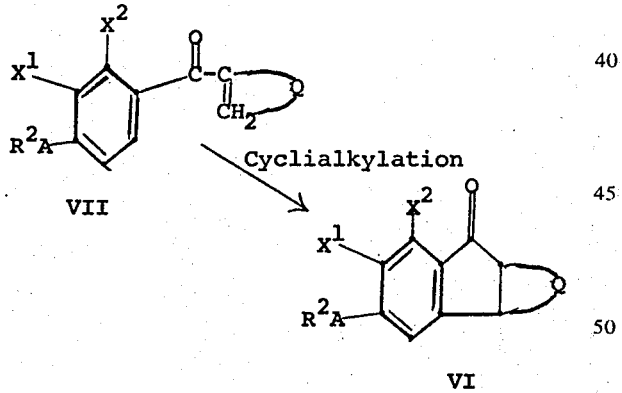

V wherein A, R, Q, $R^2$, $X^1$, $X^2$ and Z are as defined above.

One method for preparing the 2,3-hydrocarbylene-5-lower alkoxy-(and lower alkyl thio)-1-indanones (VI, supra) comprises the cyclialkylation of a nuclear lower alkoxy (or lower alkyl thio) substituted cycloalkenoylbenzene (VII, infra) by treatment with an electron-acceptor acid, for example, a Lewis acid such as concentrated sulfuric acid, polyphosphoric acid, boron trifluoride and the like. The reaction may be conducted at a temperature in the range of from about 0° to about 60°C. In general, the reaction is conducted at ambient temperature. The following equation illustrates this process:

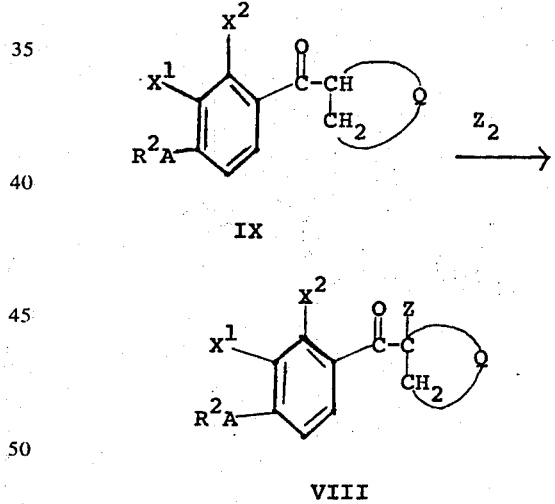

wherein A, $R^2$, Q, $X^1$ and $X^2$ are as defined above.

The nuclear lower alkoxy (and lower alkyl thio) cycloalkenoyl benzenes (VII, supra) employed above may be prepared by treating a nuclear lower alkoxy-(or lower alkyl thio)-substituted-2-halocycloakanoylbenzene (VIII, infra) with a dehydrohalogenating agent such as lithium bromide, lithium chloride and the like. Suitable solvents for this reaction include dimethylformamide and the like. This reaction is conveniently conducted at a temperature in the range of from about 50° to about 120°C. for a period of time of from about one hour to about six hours. The following equation illustrates this reaction:

wherein A, Q, $R^2$, $X^1$ and $X^2$ are as defined above.

The nuclear lower alkoxy (or lower alkyl thio) substituted (2-halocycloalkanoyl)benzenes (VIII, supra) are prepared by treating a nuclear lower alkoxy (or lower alkyl thio) substituted cycloalkanoyl benzene (IX, infra) with a halogenating agent such as bromine, chlorine, sulfuryl chloride and the like. Suitable solvents for this reaction include acetic acid, chloroform and the like. This reaction is conveniently conducted at temperatures from about 0°c. to the reflux temperature of the solvent employed for a period of time from about one-half to about two hours. The following equation illustrates this reaction:

wherein A, Q, $R^2$, $X^1$, $X^2$ and Z are as described above.

The [4-nuclear lower alkoxy (and lower alkyl thio) substituted] cycloalkanoyl benzenes (IX) are either known compounds or may be prepared by the reaction of an cycloalkanoyl halide with a nuclear lower alkoxy (or lower alkyl thio) substituted benzene (X, infra) in the presence of a Friedel-Crafts catalyst such as aluminum chloride and the like. The reaction solvent and the temperature at which the reaction is conducted are not particularly critical aspects of this reaction inasmuch as any solvent which is inert to the acyl halide and nuclear lower alkoxy (or lower alkyl thio) substituted benzenes may be employed with good results. In this regard, it has been found that methylene chloride is a particularly suitable solvent. The following equation illustrates this reaction:

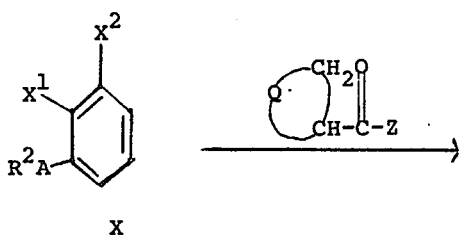

X

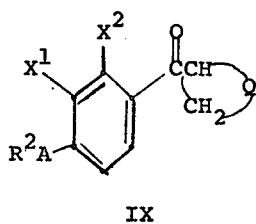

IX wherein A, Q, $R^2$, $X^1$, $X^2$ and Z are as defined.

Also included within the scope of this invention are the ester and amide derivatives of the instant products which are prepared by conventional methods well known to those skilled in the art. Thus, for example, the ester derivative may be prepared by the reaction of the substituted [1-oxo-2,3-hydrocarbylene-5-indanyloxy-(and thio)]alkanoic acids (1) of this invention as shown in compound (X) with an alcohol, for example, with a lower alkanol, $R^{10}$ OH. The amide derivatives (XII) may be prepared by converting compound (X) to its corresponding acid chloride (XI) by treatment with thionyl chloride followed by treating said acid chloride with ammonia, and appropriate monolower alkyl amide, di-lower alkyl amide, or a hetero amine, such as piperidine, morpholine and the like to produce the corresponding amide compound. These and other equivalent methods for the preparation of the ester and the amide derivatives of the [1-oxo-2,3-hydrocarbylene-5-indanyloxy(or thio)]alkanoic acids of this invention will be apparent to one having ordinary skill in the art and to the extent that said derivatives are both nontoxic and physiologically acceptable to the body system, said derivatives are the functional equivalent of the corresponding acids.

wherein $R^{10}$ is lower alkyl; $R^{11}$ is hydrogen or lower alkyl; $R^{12}$ is hydrogen, lower alkyl, hydroxyalkyl, or amino alkyl; and $R^{11}$ and $R^{12}$ may be joined to form a cyclic structure with the nitrogen atom to which they are attached.

The invention, in addition to the [1-oxo-2,3-hydrocarbylene-5-indanyloxy(or thio)]alkanoic acids, salts, esters and amides includes those compounds wherein the carboxylic acid is replaced by a 5-tetrazolyl radical which are also functionally equivalent to the carboxylic acid. These tetrazole analogs are prepared as depicted in the following equation:

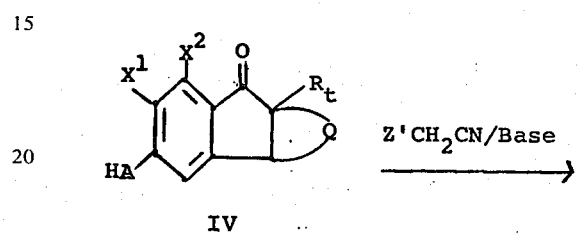

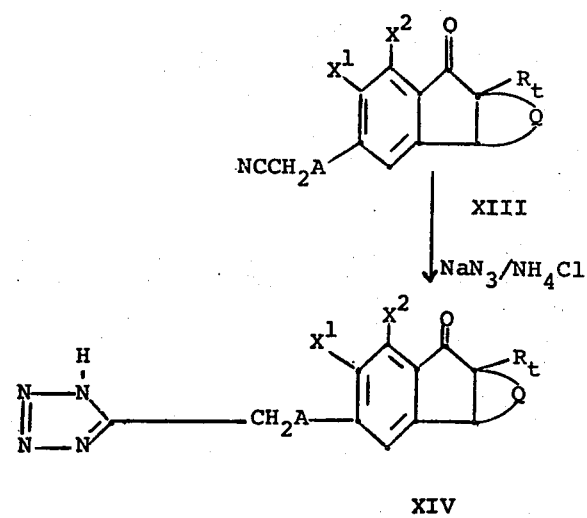

wherein all substituents are as defined above.

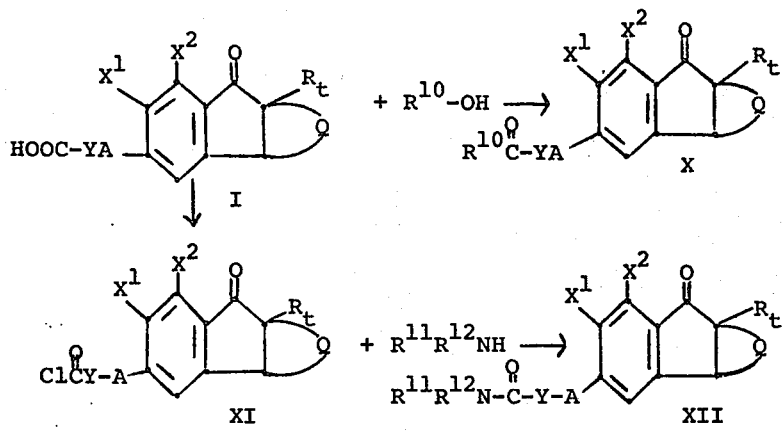

The 5-hydroxy or mercapto precursors of the instant [1-oxo-2,3-hydrocarbylene-5-indanyloxy(or thio)]alkanoic acids (IV) is treated with a haloacetonitrile such as chloroacetonitrile, bromoacetonitrile, or iodoacetonitrile in the presence of a base such as potassium carbonate and the like in a suitable solvent such as acetone, dimethylformamide, dimethoxyethane and the like at a temperature in the range of from 25° to 100°C. to afford the corresponding nitrile (XIII) which, upon treatment with sodium azide and ammonium chloride in dimethylformamide at a temperature in the range of from 25° to 100°C., affords the 5-tetrazolyl analog of the [1-oxo-2,3-hydrocarbylene-5-indanyloxy-(or thio)]acetic acid of this invention (XIV).

Many of the instant compounds (I) herein disclosed contain an assymetric carbon atom in the 2-position as illustrated:

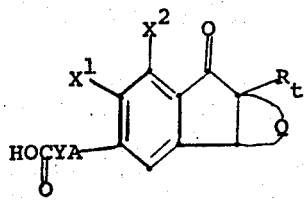

when this situation exists, the optical antipodes may be separated by methods described below. This invention embraces therefore, not only the racemic tricyclic indanes but also their optically active antipodes.

Separation of optical isomers of the racemic acids (I) may be accomplished by forming a salt of the racemic mixture with an optically active base such as (+) or (−) amphetamide, (−)-cinchonidine, dehydroabietylamine, (+) or (−)-α-methylbenzylamine, (+) or (−)-α-(1-naphthyl) ethylamine, brucine or strychnine and the like in the suitable solvents such as methanol, ethanol, 2-propanol benzene acetonitrile, nitromethane, acetone and the like. There is thus formed in the solution 2 diastereomeric salts one of which is usually more soluble as a solvent than the other. Repetitive recrystallizations of the crystalline salt generally afford a pure diastereomer. The optically pure [1-oxo-2,3-hydrocarbylene-5-indanyloxy(or thio)]alkanoic acid is obtained by acidification of the salt with a mineral acid, extraction into ether, evaporation of the solvent, recrystallization of the optically pure antipode.

The other optically pure antipode may generally be obtained by using a different base to form the diastereomeric salt. It is of an advantage to use the partially resolved acid from the filtrates of the purification of one diastereomeric salt and to further purify the substance through the use of another optically active base.

The Examples which follow illustrate the [1-oxo-2,3-hydrocarbylene-5-indanyloxy(or thio)]alkanoic acids of this invention and the methods by which they are prepared. However, the Examples are illustrative only and it would be apparent to those having ordinary skill in the art that all the products embraced by formula I may also be prepared in an analogous manner by substituting the appropriate starting materials for those set forth in the examples.

EXAMPLE 1

(1,2-Dichloro-5α-5,6,7,8,8α-hexahydro-9-oxofluoren-3-yloxy)acetic acid

Step A: Cyclohexyl (2,3-dichloro-4-methoxyphenyl) ketone

A stirred mixture of 2,3-dichloroanisole (88.5 g., 0.5 mole) and cyclohexanecarbonyl chloride (81 g., 0.55 mole) in methylene chloride (400 ml.) is cooled to 5°C. and treated with aluminum chloride (74 g., 0.55 mole) during a ½ hour period. the reaction is allowed to warm to 25°C. and after 16 hours is poured into ice-water (1 l.) and hydrochloric acid (200 ml.). The organic phase is washed with 10% sodium hydrochloride and saturated salt solution, and dried over magnesium sulfate. After evaporation of the solvent, the product is crystallized from hexane to give 42.3 g. of cyclohexyl (2,3-dichloro-4-methoxyphenyl) ketone which melts at 97°–98°C.

Elemental analysis for $C_{14}H_{16}Cl_2O_2$: Calc.: C, 58.55; H, 5.62; Found: C, 58.92; H, 5.64.

Step B: 1-Bromocyclohexyl (2,3-dichloro-4-methoxyphenyl) ketone

Bromine (22.4 g., 0.14 mole) in acetic acid (50 ml.) is added dropwise to a stirred solution of cyclohexyl(2,3-dichloro-4-methoxyphenyl)ketone (40 g., 0.14 mole) and 30% hydrobromic acid (0.5 ml.) in acetic acid (400 ml.) during a 1½ hr. period at 25°C. The mixture is poured into water (1.5 l.) and sodium bisulfite (10 g.) The product which precipitates is crystallized from cyclohexane to give 47.3 g. of 1-bromocyclohexyl (2,3-dichloro-4-methoxyphenyl) ketone which melts at 94°–95°C.

Elemental analysis for $C_{14}H_{15}BrCl_2O_2$: Calc.: C, 45.93; H, 4.13; Found: C, 45.77; H, 4.11.

Step C: 1-Cyclohexenyl (2,3-dichloro-4-methoxyphenyl) ketone

1-Bromocyclohexyl (2,3-dichloro-4-methoxyphenyl) ketone (47.3 g., 0.13 mole), lithium chloride (16.5 g., 0.39 mole) and dimethylformamide (200 ml.) are heated at 90°C. for two hours, then poured into water (1 l.) to give 36.5 g. of 1-cyclohexenyl (2,3-dichloro-4-methoxyphenyl) ketone which melts at 126°–129°C. after drying at 60°C. under vacuum for 16 hours.

Elemental analysis for $C_{14}H_{14}Cl_2O_2$: Calc.: C, 58.96; H, 4.95; Found: C, 58.87; H, 5.10.

Step D: 1α,1,2,3,4,4α-Hexahydro-6-methoxy-7,8-dichlorofluoren-9-one

A stirred mixture of 1-cyclohexenyl (2,3-dichloro-4-methoxyphenyl) ketone (34 g., 0.12 mole) and polyphosphoric acid (340 g.) is heated at 90°C. for 17 hours in a resin pot. Crushed ice (1 kg.) is added to precipitate the product which on crystallization from benzene:cyclohexane, 1:1, gives 18.4 g. of 1α,1,2,3,4,4α-hexahydro-6-methoxy-7,8-dichlorofluoren-9-one which melts at 169°–171°C.

Elemental analysis for $C_{14}H_{14}Cl_2O_2$: Calc: C, 58.96; H, 4.95; Found: C, 59.35; H, 5.43.

Step E: 1α,1,2,3,4,4α-Hexahydro-6-hydroxy-7,8-dichlorofluoren-9-one

A stirred mixture of 1α,1,2,3,4,4α-hexahydro-6-methoxy-7,8-dichlorofluoren-9-one (4.0 g., 0.014 mole) and pyridine hydrochloride (40 g.) is heated at 170°C. for 2 hours, then poured into water (800 ml.). The 1α,1,2,3,4,4α-hexahydro-6-hydroxy-7,8-dichlorofluoren-9-one which separates (3.75 g.) melts at 212°–219°C. after recrystallization from ethanol.

13

Elemental analysis for $C_{13}H_{12}Cl_2O_2$: Calc.: C, 57.58; H, 4.46; Found: C, 57.12; H, 4.53.

Step F: (1,2-Dichloro-5α,5,6,7,8,8α-hexahydro-9-oxo-fluoren-3-yloxy)acetic acid

A stirred mixture of 1α,1,2,3,4,4α-hexahydro-6-hydroxy-7,8-dichlorofluoren-9-one (3.55 g., 0.0131 mole), potassium carbonate (3.62 g., 0.0262 mole) and ethyl bromoacetate (4.37 g., 0.0262 mole) in dimethylformamide (30 ml.) is warmed at 55°–60°C. under nitrogen for three hours, then treated with potassium hydroxide (1.90 g., 0.0288 mole) in methanol (30 ml.) and heated on a steam bath for three hours. The reaction mixture is poured into water (500 ml.) and acidified with 12N hydrochloric acid to precipitate 2.00 g. to (1,2-dichloro-5α,5,6,7,8,8α-hexahydro-9-oxo-fluoren-3-yloxy)acetic acid which melts at 202°–206°C. after crystallization from acetic acid:water, 3:2.

Elemental analysis for $C_{15}H_{14}Cl_2O_4$: Calc.: C, 54.73; H, 4.29; Found: C, 54.84; H, 4.37.

EXAMPLE 2

Preparation of (1,2-dichloro-9-oxofluoren-3-yloxy)acetic acid

Step A: 1,2-Dichloro-3-methoxyfluoren-9-one

A stirred mixture of 1α,1,2,3,4,4α-hexahydro- 6-methoxy-7,8-dichlorofluoren-9-one (8.3 g., 0.029 mole), 2,3-dichloro-5,6-dicyano-1,4-benzoquinone (20.5 g., 0.091 mole), benzene (300 ml.) and acetic acid (10 ml.) is heated at reflux under nitrogen for 64 hours. The reaction mixture is dissolved in a large volume of ethyl acetate (3 l.), the organic solution treated with sodium bisulfite solution, washed with water, 5% sodium hydroxide solution and water, separated, dried over magnesium sulfate and concentrated to give 1,2-dichloro-3-methoxyfluoren-9-one which after sublimation and trituration with acetonitrile give 3.9 g. melting at 268°–270°C.

Elemental analysis for $C_{14}H_8Cl_2O_2$: Calc.: C, 60.24; H, 2.89; Found: C, 59.86; H, 3.10.

Step B: 1,2-Dichloro-3-hydroxyfluoren-9-one

A stirred mixture of 1,2-dichloro-3-methoxyfluoren-9-one (3.9 g., 0.014 mole) and pyridine hydrochloride (80 g.) is heated at 180°–190°C. (internal temperature) for 2 hours, then poured into water 1 l. The 1,2-dichloro-3-hydroxyfluoren-9-one which separates (3.25 g.) melts at 276°–284°C. and is used without further purification.

Step C: (1,2-Dichloro-9-oxo-fluoren-3-yloxy) acetic acid

A stirred mixture of 1,2-dichloro-3-hydroxyfluoren-9-one (3.0 g., 0.011 mole), potassium carbonate (3.04 g., 0.022 mole), and ethyl bromoacetate (3.68 g., 0.022 mole) in dimethylformamide (60 ml.) is warmed at 55°–60°C. for 3 hours, then treated with potassium hydroxide (1.62 g., 0.024 mole) dissolved in a minimum amount of water in methanol (60 ml.) and heated on a steam bath for 3 hours. The reaction mixture is poured into water (600 ml.) acidified with 6N hydrochloric acid and the gummy precipitate collected and crystallized from dimethylformamide:water, 3:2, to give 1.17 g. of (1,2-dichloro-9-oxo-fluoren-3-yloxy)acetic acid which melts at 305°–306°C.

Elemental analysis for $C_{15}H_8Cl_2O_4$: Calc.: C, 55.75; H, 2.49; Found: C, 55.75; H, 2.60.

14

EXAMPLE 3

[1,1α-Dihydro-4,5-dichloro-6α-isopropyl-6-oxocycloprop[α] inden-3-yloxy]acetic acid Step A: (1-Oxo-2-bromo-2-isopropyl-6,7-dichloro-5-indanyloxy)acetic acid To a stirred suspension of (1-oxo-2-isopropyl-6,7-dichloro-5-indanyloxy)acetic acid (31.5 g., 0.10 mole) in acetic acid (500 ml.) is added 5 drops of 48% HBr and then a solution of bromine (7.5 ml.) in acetic acid (30 ml.) over a 30-minute period. The orange solution is stirred for one hour at 20°–25°C. and then poured into water (2.0 l.) containing 5 g. of sodium bisulfite. (1-Oxo-2-bromo-2-isopropyl-6,7-dichloro-5-indanyloxy)acetic acid (37.1 g., 93%), m.p. 150°–153°C., separates and is used directly in the next step.

Step B: (1-Oxo-2-isopropyl-6,7-dichloroinden-5-yloxy)acetic acid (1-Oxo-2-bromo-2-isopropyl-6,7-dichloro-5-indanyloxy)acetic acid (17.3 g., 0.044 mole) is dissolved in dimethyl sulfoxide (DMSO, 100 ml.) stirred under nitrogen and 1,5-diazabicyclo[4.3.0]non-5-ene (DBN) (13 g.) is added dropwise. When the exothermic reaction ceases, the mixture is stored at 20°–25°C. for 1 1/2 hours and then poured into water (1.5 l.). The precipitate is recrystallized from acetic acid-water (1:1) to afford (1-oxo-2-isopropyl-6,7-dichloroinden-5-yloxy)acetic acid (9.6 g.), m.p. 175.5°–176°C.

Elemental analysis for $C_{14}H_{12}Cl_2O_4$: Calc.: C, 53.36; H, 3.84; Found: C, 53.55; H, 3.89.

Step C: [1,1α-Dihydro-4,5-dichloro-6α-isopropyl-6-oxocycloprop[α]-inden-3-yloxy]acetic acid (1-Oxo-2-isopropyl-6,7-dichloroinden-5-yloxy)-acetic acid (6.3 g., 0.02 mole) is dissolved in DMF (300 ml.) and sodium hydride (1.7 g., 57% in mineral oil) is added to DMF (50 ml.) and then, with cooling, trimethylsulfoxonium iodide (8.6 g.). The solutions are combined, stored at 20°–30°C. for 3½ hours, and poured into ice water (1.5 l.). The solution is extracted with hexane, acidified with 12N hydrochloric acid and extracted with ether. The ether extract is washed with water, dried (MgSO₄) and evaporated. A viscous yellow oil remains that on trituration with hexane forms a solid which is recrystallized from benzene-hexane (20:1) and butyl chloride to afford 2.0 g. of [1,1α-dihydro-4,5-dichloro-6α-isopropyl-6-oxocycloprop[α]-inden-3-yloxy] acetic acid, m.p. 133°–142°C.

Elemental analysis for $C_{15}H_{14}Cl_2O_4$: Calc. C, 54.73; H, 4.29; Found: C, 54.84; H, 4.27.

EXAMPLE 4

[1,1α-Dihydro-4,5-dichloro-6α-ethyl-6-oxocycloprop[α]inden-3-yloxy]acetic acid

A stirred solution of (1-oxo-2-ethyl-6,7-dichloroinden-5-yloxy)acetic acid (3.1 g., 0.01 mole) in DMF (20 ml.) is cooled in an ice bath and treated with sodium hydride (0.42 g. of a 57% oil dispersion, 0.01 mole). The reaction is stirred at 25°C. for 1½ hours, then treated with a solution prepared from sodium hydride (0.84 g. of a 57% oil dispersion, 0.02 mole) and trimethylsulfoxonium iodide (4.4 g., 0.02 mole) in DMF (20 ml.). After stirring for two hours, the reaction mixture is poured into water (100 ml.), extracted with hexane to remove the mineral oil, acidified with hydrochloric acid, extracted with ether which is washed with water, dried over magnesium sulfate and evaporated in vacuo affording 1.1 g. of [1,1α-dihydro-4,5-dichloro-6α-ethyl-6-oxocycloprop[α]inden-3-yloxy]acetic acid which melts at 167°C. after recrystallization from nitromethane.

Elemental analysis for $C_{14}H_{12}Cl_2O_4$: Calc.: C, 53.35; H, 3.84; Found: C, 53.02; H, 3.79.

EXAMPLE 5

(1,2-Dichloro-5α,5,6,7,8,8α-hexahydro-8α-methyl-9-oxofluoren-3-yloxy)acetic acid Step A: 1α-Methyl-1α,1,2,3,4,4α-hexahydro-6-methoxy-7,8-dichloro-fluoren-9-one Potassium tert.-butoxide (8.95 g., 0.080 mole) in tert-butanol (200 ml.) is added to a refluxing solution of 1α,1,2,3,4,4α-hexahydro-6-methoxy-7,8-dichloro-fluoren-9-one (15.2 g., 0.053 mole) in dry benzene (200 ml.) and tert-butanol (25 ml.) under nitrogen. The solution is heated at reflux for one half hour, cooled, methyl iodide (17.0 ml., 0.27 mole) is added, and the mixture brought to reflux and then cooled. Water (50 ml.) is added and on concentrating the mixture to dryness, 12.4 g. of 1α-methyl-1α,1,2,3,4,4α-hexahydro-6-methoxy-7,8-dichlorofluoren-9-one is obtained which melts at 94°–95°C. on crystallization from acetic acid.

Elemental analysis for $C_{15}H_{16}Cl_2O_2$: Calc: C, 60.21; H, 5.39; found: C, 60.44; H 5.66.

Step B: 1α-Methyl-1α,1,2,3,4,4α-hexahydro-6-hydroxy-7,8-dichlorofluoren-9-one

A stirred mixture of 1α-methyl-1α,1,2,3,4,4α-hexahydro-6-methoxy-7,8-dichlorofluoren-9-one (12.2 g., 0.041 mole) and pyridine hydrochloride (120 g.) is heated at 170°C. for 3 hours, then poured into water (1 l.). The 1α-methyl-1α,1,2,3,4,4α-hexahydro-6-hydroxy-7,8-dichlorofluoren-9-one which separates (9.7 g.) melts at 217°–219.5°C. after recrystallization from ethanol.

Elemental analysis for $C_{14}H_{14}Cl_2O_2$: Calc.: C, 58.96; H, 4.95; Found: C, 59.59; H, 5.32.

Step C: (1,2-Dichloro-5α,5,6,7,8,8α-hexahydro-8α-methyl-9-oxo-fluoren-3-yloxy)acetic acid A stirred mixture of 1α-methyl-1α,1,2,3,4,4α-hexahydro-6-hydroxy-7,8-dichlorofluoren-9-one (2.85 g., 0.01 mole), potassium carbonate (2.76 g., 0.02 mole) and ethylbromoacetate (3.34 g., 0.02 mole) in dimethylformamide (30 ml.) is warmed at 55°–60°C. for three hours, then treated with potassium hydroxide (1.45 g., 0.022 mole) dissolved in a minimum amount of water in methanol (30 ml.) and heated on a steam bath for three hours. The reaction mixture is poured into water (500 ml.), acidified with 12N hydrochloric acid to precipitate a gummy product. The product is taken up in ether, dried, concentrated, triturated with hexane, and crystallized from acetic acid:water, 3:2, to give 2.22 g. of (1,2-dichloro-5α,5,6,7,8,8α-hexahydro-8α-methyl-9-oxo-fluoren-3-yloxy)acetic acid which melts at 159°–161°C.

Elemental analysis for $C_{16}H_{16}Cl_2O_4$: Calc.: C, 55.99; H, 4.70; Found: C, 56.06; H, 4.74.

The novel compounds of this invention are diuretic and saluretic agents. In addition, these compounds are also able to maintain the uric acid concentration in the blood at pretreatment levels or even cause a decrease in uric acid concentration. The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a [1-oxo-2,3-hydrocarbylene-5-indanyloxy(or thio)] alkanoic acids, particularly the compounds of formula I or a suitable salt, ester or amide derivative thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods, and if desired, can be made up as elixirs or as injectable solutions by methods well known to pharmacists. An effective amount of the drug is ordinarily supplied at a dosage level of from about 1 mg. to about 50 mg./kg. of body weight. Preferably the range is from about 0.1 mg. to 7 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following example is included to illustrate the preparation of a representative dosage form

EXAMPLE 6

Dry-filled capsules containing 50 mg. of active ingredient per capsule

|  | Per Capsule |
| --- | --- |
| (1,2-Dichloro-5α,5,6,7,8,8α-hexahydro-8α-methyl-9-oxo-fluoren-3-yloxy)acetic acid | 50 mg. |
| Lactose | 149 mg. |
| Magnesium Stearate | 1 mg. |
| Capsule (Size No. 1) | 200 mg. |

The (1,2-dichloro-5α,5,6,7,8,8α-hexahydro-8α-methyl-9-oxofluoren-3-yloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the [1-oxo-2,3-hydrocarbylene-5-indanyloxy(or thio)] alkanoic acids of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula:

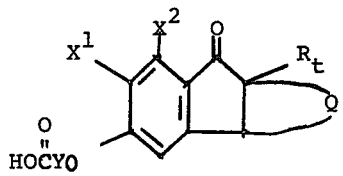

wherein
 $X^1$ is hydrogen, halogen or methyl;
 $X^2$ is halogen, methyl or trifluormethyl;
 Y is alkylene or haloalkylene containing a maximum of 4 carbon atoms;
 R is hydrogen or loweralkyl;
 $t$ is an integer having a value of 1;
 Q is a saturated hydrocarbylene bridge containing together with the carbon atoms of the indane nucleus to which they are attached from 3 to 6 carbon atoms;
and the non-toxic pharmaceutically acceptable salt and lower-alkyl ester derivative thereof.

2. A compound of the formula

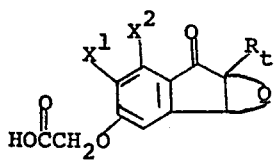

wherein
 $X^1$ is hydrogen, methyl or chloro;
 $X^2$ is methyl or chloro;
 R is hydrogen or loweralkyl;
 $t$ is an integer having a value of 1;
 Q is a hydrocarbylene radical selected from the group consisting of methylene, ethylene, trimethylene and tetramethylene;
and the pharmaceutically acceptable salts thereof.

3. A compound of claim 2 wherein
 $X^1$ is chloro;
 $X^2$ is chloro;
 R is methyl;
 Q is tetramethylene;
which is (1,2-dichloro-5α,5,6,7,8,8α-hexahydro-8α-methyl-9-oxofluoren -3-yloxy)-acetic acid.

4. A compound of claim 2 wherein
 $X^1$ is chloro;
 $X^2$ is chloro;
 R is hydrogen;
 Q is tetramethylene;
which is (1,2-dichloro-5α,5,6,7,8,8α-hexahydro-9-oxofluoren-3-yloxy)-acetic acid.

5. A compound of claim 2 wherein
 $X^1$ is chloro;
 $X^2$ is chloro;
 R is isopropyl;
 Q is methylene;
which is [1,1α-dihydro-4,5-dichloro-6α-isopropyl-6-oxocycloprop[α]-inden-3-yloxy]acetic acid.

6. A compound of claim 2 wherein
 $X^1$ is chloro;
 $X^2$ is chloro;
 R is ethyl;
 Q is methylene;
which is [1,1α-dihydro-4,5-dichloro-6α-ethyl-6-oxocycloprop[α]inden-3-yloxy]acetic acid.

* * * * *